United States Patent
Heinz et al.

(10) Patent No.: US 10,637,930 B2
(45) Date of Patent: Apr. 28, 2020

(54) SYSTEM FOR INTEGRATING A DETECTABLE MEDICAL MODULE

(71) Applicant: Foundry Health, Grafton, WI (US)

(72) Inventors: Brock Heinz, Grafton, WI (US); Stuart D. Robertson, II, Chicago, IL (US)

(73) Assignee: Foundry Health, Chicago, IL (US)

( * ) Notice: Subject to any disclaimer, the term of this patent is extended or adjusted under 35 U.S.C. 154(b) by 83 days.

(21) Appl. No.: 15/676,539

(22) Filed: Aug. 14, 2017

(65) Prior Publication Data

US 2019/0052710 A1 Feb. 14, 2019

(51) Int. Cl.
*H04L 29/08* (2006.01)
*G16H 40/20* (2018.01)
*G16H 40/67* (2018.01)

(52) U.S. Cl.
CPC .......... *H04L 67/14* (2013.01); *G16H 40/20* (2018.01); *G16H 40/67* (2018.01); *H04L 67/025* (2013.01); *H04L 67/12* (2013.01); *H04L 67/16* (2013.01); *H04L 67/303* (2013.01)

(58) Field of Classification Search
None
See application file for complete search history.

(56) References Cited

U.S. PATENT DOCUMENTS

| | | |
|---|---|---|
| 5,956,483 A | 9/1999 | Grate et al. |
| 8,225,015 B2 * | 7/2012 | Gao-Saari ............. G06F 13/102 710/64 |
| 9,270,726 B2 | 2/2016 | Keskitalo et al. |
| 9,420,040 B2 | 8/2016 | Chen |
| 9,619,307 B2 | 4/2017 | Maltese et al. |
| 2002/0178126 A1* | 11/2002 | Beck .................... A61B 5/0002 705/75 |
| 2004/0167465 A1* | 8/2004 | Mihai .................. A61B 5/0002 604/67 |

(Continued)

OTHER PUBLICATIONS

Peter Lubbers & Frank Greco, Kaazing Corporation; HTML5 WebSocket: A Quantum Leap in Scalability for the Web; https://websocket.org/quantum.html—(8) pages.

*Primary Examiner* — Clayton R Williams
*Assistant Examiner* — Tania M Pena-Santana
(74) *Attorney, Agent, or Firm* — Boyle Fredrickson, S.C.

(57) ABSTRACT

Medical devices and other modules configured in local computing environments can be detected, remotely managed, and integrated with a web application hosted on a server using standard communication protocols and a local agent. Such modules can include hardware devices, such as electrocardiograph (ECG) machines, centrifuges and the like, and/or software modules, such as Electronic Medical Records (EMR). The modules can be detected by a web browser receiving input which can be configured to be initiated by a sensor and/or Application Program Interface (API). The web browser, in turn, can communicate with the remote server for approval of the module. Upon approval, the server can establish a WebSocket communication channel through the browser to an agent executing in the local environment. The server can then push a device profile and/or commands to the agent, including a command to execute source code, and the agent, in turn, can collect data from, and/or execute commands with respect to, the module.

22 Claims, 3 Drawing Sheets

(56) References Cited

U.S. PATENT DOCUMENTS

| | | | | |
|---|---|---|---|---|
| 2005/0228693 A1* | 10/2005 | Webb | ................ | G06Q 50/22 |
| | | | | 705/2 |
| 2006/0218016 A1* | 9/2006 | Hohn | ................ | G06Q 10/10 |
| | | | | 705/4 |
| 2009/0158274 A1* | 6/2009 | Roberts | ................ | G16H 40/40 |
| | | | | 717/178 |
| 2013/0087609 A1* | 4/2013 | Nichol | ................ | G06Q 10/087 |
| | | | | 235/375 |
| 2013/0312066 A1* | 11/2013 | Suarez | ................ | G16H 40/67 |
| | | | | 726/4 |
| 2014/0143386 A1 | 5/2014 | Sokoryansky | | |
| 2014/0266794 A1* | 9/2014 | Brown | ................ | G16H 40/67 |
| | | | | 340/870.16 |
| 2015/0143467 A1 | 5/2015 | Hebert et al. | | |

* cited by examiner

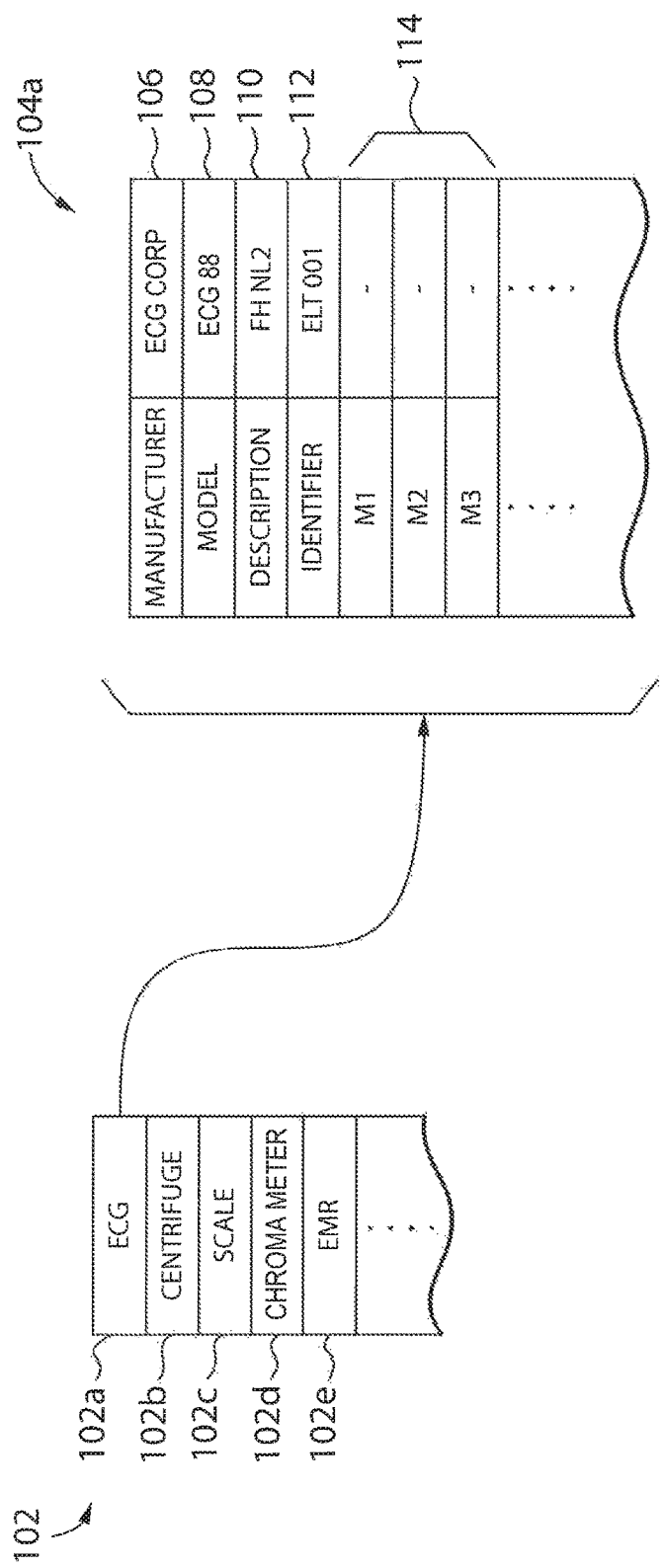

SYSTEM FOR INTEGRATING A DETECTABLE MEDICAL MODULE

FIELD OF THE INVENTION

The present invention relates to the field of communications between medical modules, and more particularly, to a system for integrating a detectable medical module using a web browser executing a web page configured to detect a presence of a detectable medical module and a local agent in communication with the web browser.

BACKGROUND OF THE INVENTION

Web applications typically allow complex logic and processes to be remotely accessible to local computers for achieving various functions worldwide. However, it is difficult for such applications to know the exact hardware and/or software devices being controlled by the local computers. Knowledge of such devices can enable applications to provide better management, control and/or utilization of the local computers. In the medical industry, this can mean greater consistency, reliability and/or convenience for integrating medical devices and software such as electrocardiograph (ECG) machines, centrifuges, digital scales, Electronic Medical Records (EMR's) and the like.

It is known to add custom extensions to local computers to enable discovery of devices and software for utilization by web applications. However, such extensions typically lack compatibility across different platforms and, in some cases, are vulnerable to security threats. A need therefore exists to provide a system for integrating medical devices that eliminates one or more of the foregoing disadvantages.

SUMMARY OF THE INVENTION

Medical devices and other modules configured in local computing environments can be detected, remotely managed, and integrated with a web application hosted on a server using standard communication protocols and a local agent. As used herein, a "server" is a computer system which provides a hosting context for web application logic. Such hosting can be on a specific physical or virtual system, or can be on a logical system, such as a compute cloud. The modules can include hardware devices, such as electrocardiograph (ECG) machines, centrifuges and the like, and/or software modules, such as Electronic Medical Records (EMR). The modules can be detected by a web browser receiving input which can be configured to be initiated manually or automatically by a sensor and/or Application Program Interface (API). The web browser, in turn, can communicate with the remote server for approval of the module. Upon approval, the server can establish a WebSocket communication channel through the browser to an agent executing in the local environment. The server can then push a device profile and/or commands to the agent, including a command to execute source code, and the agent, in turn, can collect data from, and/or execute commands with respect to, the module.

Accordingly, aspects of the invention can provide a mechanism for interaction between a web browser and local resources on a user's computer, such as medical devices, other software resources and other assets which are visible to the user's workstation but not from the remote web application. The mechanism can leverage browser WebSockets and a user-local web server for reliable and secure communication, with the web server providing the actual application. The browser application can rely purely on web standards, without requiring use of plug-ins, such as ActiveX, Flash, Java Applets or the like.

In one aspect, a software agent can be installed on a user's computer. This component can perform the low level integration with the externally invocable resources. The agent can expose a WebSocket interface secured with a self-signed certificate. This can allow secure communications between the user's local browser and the software agent.

In operation, a web page can be loaded from a remote web application onto a user's browser. The web page can look for a WebSocket server running on localhost (the user's computer) at a particular port and address. When the WebSocket connection is established, this can become an asynchronous, two way channel for communication between the web application and the user-local software agent. Over this channel, the agent can expose functionality allowing bidirectional interaction to resources accessible from the user's computer. The agent can interact with a variety of resources. For example, aspects of the invention can allow: invoking and reading data from locally-connected medical devices such as printers, vital sign devices, and the like; communicating with networked computing resources only available to the user's computer; leveraging local resource polling for files, to drives visible from the user's computer; invoking API's of locally-accessible services such as ECG systems; and combinations of the above, assembled by the software agent to address a wide variety of use cases. The invention allows a web application to interact with user-local resources while strictly relying on HTML web standards.

In one aspect, a sensor can be configured to initiate the communication between the browser and the agent (a WebSocket server that communicates with servers/devices connected to the data collection computer). The sensor could be a barcode scanner. In one instance, scanning a barcode could be required before a device could be used. This can provide traceability, for example, when users/regulators view data that has been acquired for a given medical test. In addition, the system can globally qualify or disqualify individual devices based on settings in the server. A device can be disqualified by ensure it is not marked "Approved," or can be disqualified if the date in which it is being used is outside of a calibration window. Also, both configuration and actual source code can be pushed down from the server to the agent.

Specifically then, one aspect of the present invention can provide a system for integrating a detectable medical module, the system including: a host computer configured to execute: (a) a web browser executing a web page configured to detect a presence of a detectable medical module; and (b) a local agent in communication with the web browser. Detection of a medical module by the web browser can cause the web browser to communicate with a web server to obtain approval or disapproval for the detectable medical module. Approval of the detectable medical module can cause the local agent to load a device profile having multiple fields corresponding to the detectable medical module and can cause the local agent to collect data from the detectable medical module corresponding to the multiple fields.

Another aspect of the present invention can provide a method for integrating a detectable medical module, the method including: executing on a host computer: (a) a web browser executing a web page configured to detect a presence of a detectable medical module; and (b) a local agent in communication with the web browser; upon detecting a presence of a detectable medical module by the web browser, causing the web browser to communicate with a web server to obtain approval or disapproval for the detectable medical module; and upon approval of the detectable medical module, causing the local agent to load a device profile having multiple fields corresponding to the detectable medical module and causing the local agent to collect data from the detectable medical module corresponding to the multiple fields.

These and other objects, advantages and aspects of the invention will become apparent from the following description. The particular objects and advantages described herein can apply to only some embodiments falling within the claims and thus do not define the scope of the invention. In the description, reference is made to the accompanying drawings which form a part hereof, and in which there is shown a preferred embodiment of the invention. Such embodiment does not necessarily represent the full scope of the invention and reference is made, therefore, to the claims herein for interpreting the scope of the invention.

BRIEF DESCRIPTION OF THE DRAWINGS

Preferred exemplary embodiments of the invention are illustrated in the accompanying drawings in which like reference numerals represent like parts throughout, and in which:

FIG. 3 is an exemplar approval list for the system of FIG. 1; and

FIG. 4 is an exemplar set of device classes and profiles for the system of FIG. 1.

DETAILED DESCRIPTION OF THE OF THE INVENTION

Figure 1:
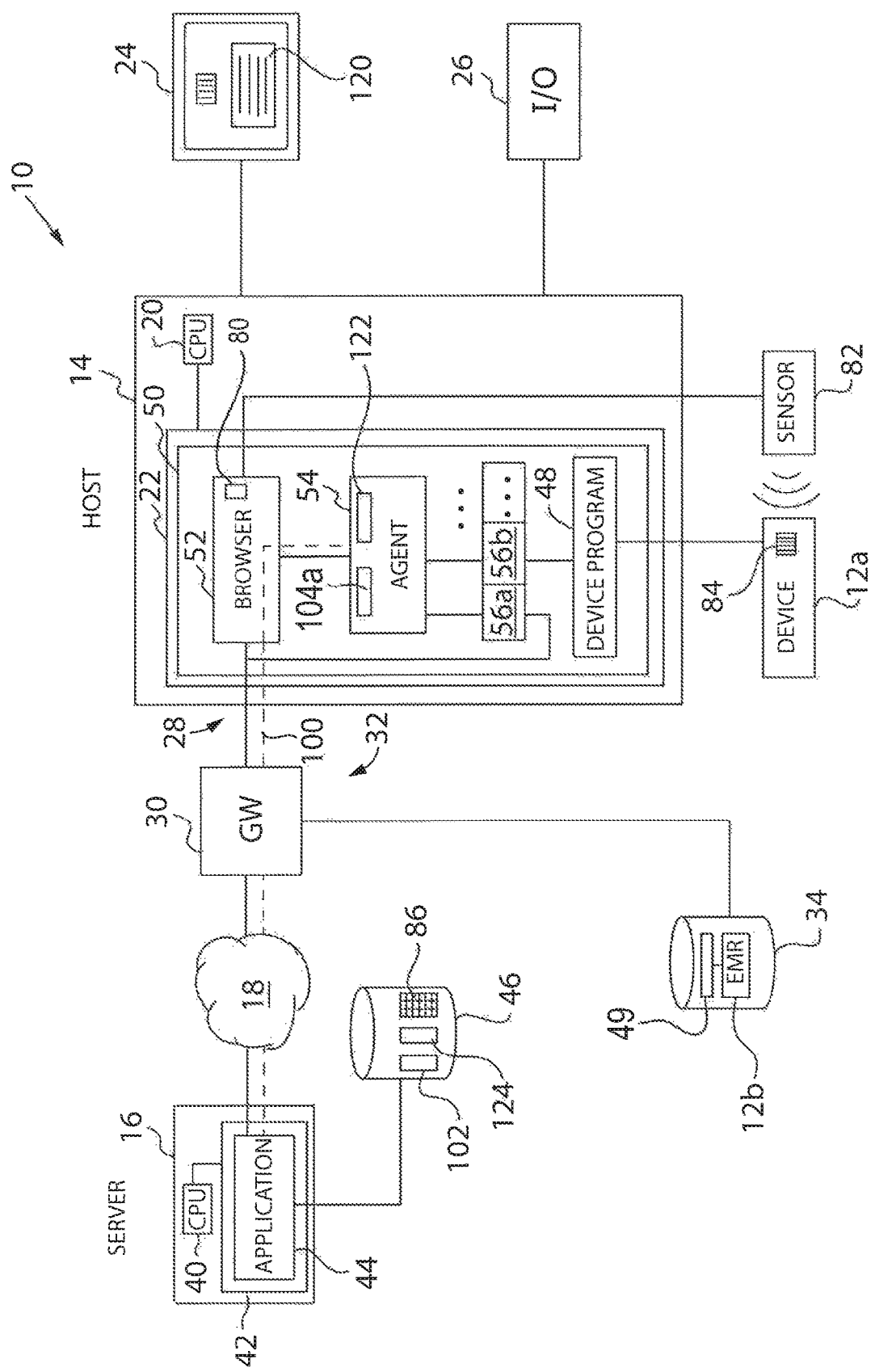
FIG. 1 is a block diagram illustrating a system for integrating a detectable medical module in accordance with an aspect of the invention.

Referring now to FIG. 1, a block diagram illustrating a system 10 for integrating detectable medical modules 12 is provided in accordance with an aspect of the invention. The system 10 can include a host computer 14 in communication with a server 16 via a first network 18, which could be a Wide Area Network (WAN) such as the Internet. The host computer 14 can include a processor 20 configured to execute programs stored in a non-transient media 22. The host computer 14 can be connected to a monitor or other visual display 24, a user I/O 26, which can include a keyboard, mouse and/or touchscreen, and a network interface 28 for communicating with a network access device 30, such as a gateway or router. Through the network access device 30, the host computer 14 can communicate over the first network 18, including with the server 16, and/or over a second network 32, such as a wired or wireless Local Area Network (LAN), for accessing local computing devices, such as a local data structure 34.

The server 16 can include a processor 40 configured to execute programs stored in a non-transient media 42. In particular, the server 16 can execute a web application 44 for configuring and managing the detectable medical modules 12 as will be described herein. The server 16 can be connected to a server data structure 46 for accessing data in support of the configuration and management functions as will be described herein.

The system 10 can be configured to integrate a variety of detectable medical modules 12, particularly in the medical device field. A first category of detectable medical modules 12 can include physical hardware devices, such as electrocardiograph (ECG) machines for recording electrical activity of a patient's heart over a period of time, centrifuges for rotating an object around a fixed axis to isolate and/or separate biological materials, digital scales for measuring a patient's physical characteristics, such as height and weight, chroma meters for measuring color of objects, such as a patient's skin, using light, and the like. These hardware devices can be can be in communication with the host computer 14 directly, such as via Bluetooth, USB or other serial communication, or indirectly, such as via the second network 32. In addition, these hardware devices can be logically controlled by local or remote device programs which can include drivers, execution logic and/or Graphical User Interfaces (GUI's). For example, detectable medical module 12a, which is physically connected to the host computer 14, is an example of a detectable medical module 12 that can be a hardware device that is logically controlled by local device program 48.

A second category of detectable medical modules 12 can include software modules, such as Electronic Medical Records (EMR) and the like. These software modules can be accessed by the host computer 14, such as in the non-transient media 22, or elsewhere in the system 10, such as the local data structure 34. In other words, the software module could be on the host computer 14, or it could be on the LAN (the second network 32) and reachable by the host computer 14, such as through a remote device program 49. Detectable medical module 12b is an example of a detectable medical module 12 that can be a software module.

To integrate a detectable medical module 12, the host computer 14 can execute multiple programs in conjunction with an operating system 50, including a web browser 52, a local agent 54, and one or more Application Program Interfaces (API's) 56. With additional reference to FIG. 2, a process flow diagram 60 is provided illustrating operation of the system 10 in accordance with an aspect of the invention. At step 62, the web browser 52 can execute a web page 80 (FIG. 1) configured to detect a presence of a detectable medical module 12. The web page 80 can be configured, for example, to implement JavaScript rules downloaded from the web application 44 hosting the web page 80. In one aspect, a sensor 82 connected to the host computer 14 can be used to manually or automatically sense an indicium 84 corresponding to the detectable medical module 12a. The sensor 82 could be, for example, a barcode scanner or Radio-Frequency Identification (RFID) reader, or the like, operated by a user, and the indicium 84 could be, for example, a barcode, a QR code, an RFID tag, or the like. However in another aspect, an API 56 executing on the host computer 14 can be used to locate a detectable medical module 12, such as a first API 56a being configured to locate the remote device program 49 and, in turn, the detectable medical module 12b, or a second API 56b being configured to locate the local device program 48 and, in turn, the detectable medical module 12a. With the web page 80 active, a module identifier corresponding to a sensed or located detectable medical module 12 can then be communicated to the web browser 52 for detecting a presence of the detectable medical module 12.

Next, upon receiving a module identifier, the web browser 52 can determine whether a presence of a detectable medical module 12 is detected. In one aspect, the web page 80 can be configured to detect a presence of a detectable medical module 12, such as a hardware device, by monitoring for entry of a character string having one or more predetermined features. Such predetermined features can include, for example, alphanumeric patterns, symbols, carriage returns or the like substantially matching a reference pattern stored in a look up table or as a calculated hash value, receiving the character string within a maximum amount of time, such as 100 milliseconds, which may be a rate that is faster than a user would likely have manually typed the character string, and/or combinations thereof. In another aspect, the web page 80 can be configured to detect a presence of a detectable medical module 12, such as a software module, by executing an API 56. The API 56 could monitor, for example, for particular module identifiers having one or more of the aforementioned predetermined features, with instances of such identifiers causing the API 56 to communicate the identifier to the web browser 52.

In another aspect, at step 62, as another type of sensor, a user can select an icon on the web page 80 to initiate capture of a detectable medical device 12. Such selection can then be communicated to the agent 54 which, in turn, can execute to detect a presence of a detectable medical module 12, such as by executing the API 56.

Next, at step 64, upon the web browser 52 detecting a presence of a detectable medical module 12 as described above, the web browser 52 can proceed to communicate with the server 16 to obtain approval or disapproval for the detectable medical module 12. The server 16, executing the web application 44, can reference a data structure 86 for approval, stored in the server data structure 46. The data structure 86 could comprise, for example, a look up table, a Structured Query Language (SQL) Relational Database Management System (RDMS), a non-relational SQL ("NoSQL") system, or any other mechanism known in the art. With additional reference to FIG. 3, an exemplar data structure 86 can include multiple fields for a verifying, and ultimately approving, a detectable medical module 12. Fields of the data structure 86 can include, for example: a class field 90 for identifying a category to which devices belong (such as an "ECG" machine); an identifier field 92 for identifying particular detectable medical modules 12 within a class (such as "ELT 001"); a location field 94 for identifying a physical location (such as an address or GPS coordinates), custodian (such as a particular hospital or research facility), and/or project (such as particular clinical study) for the particular detectable medical modules 12 (such as "FH NL2"); an approval field 96 for identifying whether the particular detectable medical modules 12 is currently approved for integration and use or disapproved (such as "Yes," indicating the device is currently approved); and/or a calibration field 98 for identifying whether the particular detectable medical modules 12 is currently in a valid condition for use, such as having completed proper calibration within a specified time period (such as "Yes," indicating the device is within a currently calibration window).

Controlling approval (and conversely, disapproval) of detectable medical modules 12 at the server 16 can be useful for ensuring that correct devices are used for correct purposes. For example, operating a high speed centrifuge in a first clinical project may be necessary, whereas operating the high speed centrifuge in a second clinical project may be catastrophic. Moreover, tracking calibration of detectable medical modules 12 at the server 16 can be useful for ensuring that only devices meeting required specifications are used.

Next, at step 66, the server 16 can indicate approval or disapproval for the detectable medical module 12, as determined from the approval field 96 and/or the calibration field 98, which may be sent to the visual display 24. If the server 16 is providing approval, at step 68, the server 16 can proceed to establish a dedicated communication channel 100 to the local agent 54. The local agent 54 can be configured to communicate with the web browser 52 over local host ("localhost") server. Accordingly, the communication channel 100 can be a dedicated WebSocket communication channel providing full-duplex communication over a Transmission Control Protocol (TCP) connection through the web browser 52.

In addition, at step 68, the server 16 can prepare a device profile and/or commands, including source code for the detectable medical module 12 to execute, corresponding to the detectable medical module 12 for sending to the local agent 54 via the communication channel 100. As used herein, a "device profile" refers to a data file having multiple data fields that are operable to characterize a particular to a device type. For example, a device profile for an ECG machine might have a data field characterizing, among other things, a heart rate measurement, whereas a device profile for a centrifuge might have a data field characterizing, among other things, an angular velocity. With additional reference to FIG. 4, an exemplar set of device classes 102, and an exemplar device profile 104a from among many device profiles 104 which could correspond to exemplar device class 102a, are provided. In one aspect, the device classes 102 and/or device profiles 104 can be stored in the server data structure 46. A device class 102 can define multiple fields corresponding to a detectable medical module 12 of a particular type. Different device classes can exist for different detectable medical modules 12, such as ECG machine device class 102a, a centrifuge device class 102b, a digital scale device class 102c, a chroma meter device class 102d, an EMR device class 102e, and so forth. Accordingly, in one aspect, device classes 102 can be arranged according to the types of data fields that might be common within a class.

Shown by way of example, if the detectable medical module 12 is an ECG machine corresponding to the device class 102a, a device profile 104 can be prepared for the detectable medical module 12. In this case, device profile 104a can be prepared having fields corresponding to the detected ECG machine, such as: a manufacturer field 106 for identifying a manufacturer of the ECG machine (such as "ECG Corp."); a model field 108 for identifying a model number for the ECG machine (such as "ELI"); a description field 110 for identifying a description for ECG machine, such as a location, custodian and/or project (such as "FH NL2"); an identifier field 112 for identifying a module identifier for the ECG machine (such as "ECG 88"); and one or more measurement fields 114 for identifying data collected from the ECG machine, such as a PR interval, a QT duration, a corrected QT (QTc) duration, a PR axis, a QRS axis, and so forth. It will be appreciated that other detectable medical module 12 can have other configurations for device profiles 104 according to their device class 102. For example, a device profile for the detectable medical module 12b, which may be an EMR, can have various fields, including measurement values, corresponding to aspects of the EMR, such as a patient's demographics, medical history, medication and allergies, immunization status, laboratory test results, radiology images, vital signs, personal statistics such as height, weight and age, and/or billing information.

The device profile 104, corresponding to the detectable medical module 12, can be pushed to the local agent 54 via the communication channel 100. Accordingly, the local agent 54 can load the device profile 104, and, at step 70, the local agent 54 can initiate communication with the detectable medical module 12 to query the detectable medical module 12 for measurements. For example, for the detectable medical module 12a being a hardware device, such as an ECG, the local agent 54 can communicate with the local device program 48 via the second API 56b. However, for the detectable medical module 12b being a software module, such as an EMR, the local agent 54 can communicate with the local data structure 34 and, in turn, the detectable medical module 12b via the first API 56a. Then, at step 72, the local agent 54 can collect the measurements from the detectable medical module 12 and populate the fields of the device profile 104.

In addition, or alternatively, the device profile 104 can include predetermined parameters to be pushed to a detectable medical module 12. For example, a device profile 104 corresponding to the detectable medical module 12b, which could be an EMR, could have various predetermined and/or acquired parameters for a particular patient, such as laboratory test results, demographics, and the like, pushed to corresponding parameters of the detectable medical module 12 for that patient. Accordingly, parameters acquired by the local agent 54 for a first detectable medical module 12a, such as the ECG as described above, could then pushed to corresponding parameters of the second detectable medical module 12b, such as the EMR, via the local agent 54. In this way, the system 10 can advantageously detect a first detectable medical module 12a, associate the first detectable medical module 12a with a second detectable medical module 12b, such as by corresponding the detectable medical modules to a common identifier in their respective device profiles 104, then acquire a parameter of the first detectable medical module 12a, and then transfer the acquired parameter to the second detectable medical module 12b.

Finally, at step 74, the local agent 54 can send the collected data to various locations as desired. In a preferred instance, the local agent 54 can send the collected data from the detectable medical module 12 to the server 16 for processing so that the web application 44 can send particular commands, including source code, as will be described herein. In another instance, the local agent 54 can send the collected data from the detectable medical module 12 to the visual display 24 in graphic form 120, so that the measurements and/or other fields of the populated device profile 104 can be displayed to a user. In yet another instance, the local agent 54 can send the collected data from the detectable medical module 12 to the local data structure 34 for archival.

Figure 2:
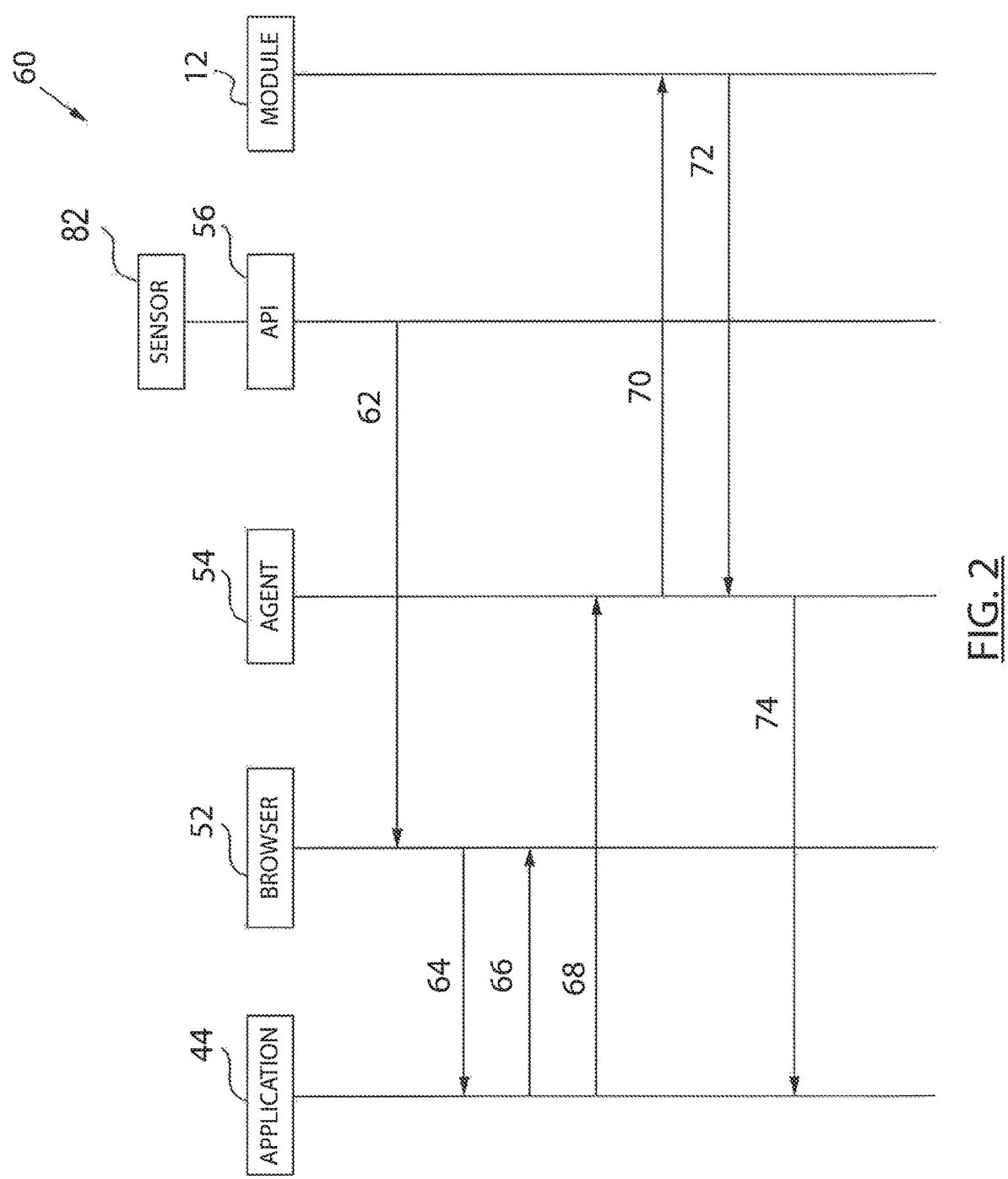
FIG. 2 is process flow diagram which can be implemented in the system of FIG. 1.

Referring still to FIG. 2, according to another aspect of the invention, at step 68, in addition to the server 16 pushing the device profile 104 to the local agent 54, the server 16 can also push commands 122, generated by a rules engine 124, to the local agent 54, via the communication channel 100. The local agent 54, in turn, can execute such commands 122 for integrating the detectable medical module 12. In one aspect, the command 122 can include receiving source code in the form of a set of instructions from the server 16, compiling the set of instructions using resources of the host computer 14, and executing the compiled set of instructions. This can be useful to dynamically cause a desired result with respect to the detectable medical module 12, such as reinitializing hardware, updating firmware, modifying data fields, and the like. In another aspect, the command 122 can include selecting between executing a first set of instructions or a second set of instructions with respect to the detectable medical module 12. This can be useful, for example, to dynamically implement a branching logic path at the local agent 54 depending on various criteria. In yet another aspect, the command 122 can include sending information to the visual display 24. This can be useful, for example, to dynamically display to a user various information, such as graphical representation of the indicium 84 or the detectable medical module 12. Accordingly, medical devices and other modules in the environment of the host computer 14 can be detected and remotely managed by the server 16 using standard communication protocols and the local agent 54.

Certain terminology is used herein for purposes of reference only, and thus is not intended to be limiting. For example, terms such as "upper," "lower," "above," and "below" refer to directions in the drawings to which reference is made. Terms such as "front," "back," "rear," "bottom," "side," "left" and "right" describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first," "second" and other such numerical terms referring to structures do not imply a sequence or order unless clearly indicated by the context.

When introducing elements or features of the present disclosure and the exemplary embodiments, the articles "a," "an," "the" and "said" are intended to mean that there are one or more of such elements or features. The terms "comprising," "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

It is specifically intended that the present invention not be limited to the embodiments and illustrations contained herein and the claims should be understood to include modified forms of those embodiments including portions of the embodiments and combinations of elements of different embodiments as coming within the scope of the following claims. All of the publications described herein including patents and non-patent publications are hereby incorporated herein by reference in their entireties.

What is claimed is:

1. A system for integrating a detectable medical module, the system comprising:
   a host computer configured to execute:
      a web browser executing a web page configured to detect a presence of a detectable medical module; and
      a local agent in communication with the web browser,
   wherein detection of a presence of a detectable medical module by the web browser causes the web browser to communicate with a web server to obtain approval or disapproval for integration of the detectable medical module in a medical system,
   wherein the approval or disapproval is obtained by the web server referencing a data structure comprising first plurality of fields, including at least one field indicating the approval or disapproval for the detectable medical module, and
   wherein upon obtaining the approval for the detectable medical module as indicated by the web server, the approval causes the local agent to load a device profile having a second plurality of fields corresponding to the detectable medical module and causes the local agent to collect data from the detectable medical module corresponding to the second plurality of fields so that the detectable medical module is integrated in the medical system.

2. The system of claim 1, further comprising, upon approval of the detectable medical module, the local agent executing a command received by the web server for integrating the detectable medical module.

3. The system of claim 2, wherein the command comprises receiving, compiling and executing a set of instructions.

4. The system of claim 2, wherein the command comprises selecting between executing a first set of instructions or a second set of instructions.

5. The system of claim 2, further comprising a visual display, wherein the command comprises sending a barcode corresponding to the detectable medical module to the visual display.

6. The system of claim 1, wherein the local agent is configured to communicate with the web browser over local host via a WebSocket communication channel.

7. The system of claim 1, wherein the web page is configured to detect a presence of a detectable medical module by monitoring for a character string having a predetermined feature.

8. The system of claim 7, wherein the predetermined feature comprises a pattern of the character string, a maximum time in which the character string is received, or both.

9. The system of claim 1, further comprising a barcode scanner, wherein scanning a barcode corresponding to a detectable medical module causes an identifier to be communicated to the web browser for detecting the presence of the detectable medical module.

10. The system of claim 9, wherein the detectable medical module is an electrocardiograph (ECG) machine, a centrifuge, a digital scale or a chroma meter.

11. The system of claim 10, wherein the second plurality of fields includes a measurement taken by the detectable medical module.

12. The system of claim 1, further comprising the host computer being configured to execute an Application Programming Interface (API) monitoring for detectable medical modules having identifiers, wherein detecting a detectable medical module having an identifier causes the identifier to be communicated to the web browser for detecting the presence of the detectable medical module.

13. The system of claim 12, wherein the detectable medical module is an electronic medical record (EMR).

14. The system of claim 1, further comprising a visual display, wherein the data from the detectable medical module corresponding to the second plurality of fields is sent to the visual display.

15. A method for integrating a detectable medical module, the method comprising:
executing on a host computer:
a web browser executing a web page configured to detect a presence of a detectable medical module; and
a local agent in communication with the web browser;
upon detecting a presence of a detectable medical module by the web browser, causing the web browser to communicate with a web server to obtain approval or disapproval for integration of the detectable medical module in a medical system,
wherein the approval or disapproval is obtained by the web server referencing a data structure comprising a first plurality of fields, including at least one field indicating the approval or disapproval for the detectable medical module; and
upon obtaining the approval for the detectable medical module as indicated by the web server, the approval causing the local agent to load a device profile having a second plurality of fields corresponding to the detectable medical module and causing the local agent to collect data from the detectable medical module corresponding to the second plurality of fields so that the detectable medical module is integrated in the medical system.

16. The method of claim 15, further comprising, upon approval of the detectable medical module, the local agent executing a command received by the web server for integrating the detectable medical module.

17. The method of claim 16, wherein the command comprises receiving, compiling and executing a set of instructions.

18. The method of claim 15, wherein the local agent is configured to communicate with the web browser over local host via a WebSocket communication channel.

19. The method of claim 15, further comprising scanning a barcode corresponding to a detectable medical module causes an identifier to be communicated to the web browser for detecting the presence of the detectable medical module.

20. The method of claim 15, further comprising the host computer being configured to execute an Application Programming Interface (API) monitoring for detectable medical modules having identifiers, wherein detecting a detectable medical module having an identifier causes the identifier to be communicated to the web browser for detecting the presence of the detectable medical module.

21. The system of claim 1, wherein the at least one field of the first plurality of fields is an approval field which indicates whether the detectable medical module is currently approved for use.

22. The system of claim 1, wherein the at least one field of the first plurality of fields is a calibration field indicating whether the detectable medical module is in a valid condition for use.

* * * * *